United States Patent
Doh et al.

(10) Patent No.: US 8,940,489 B2
(45) Date of Patent: Jan. 27, 2015

(54) MONOCLONAL ANTIBODY AGAINST D-DIMER AND DIAGNOSIS AGENT FOR DETECTING D-DIMER, CROSSLINKED FIBRIN AND ITS DERIVATIVES CONTAINING D-DIMER BY USING THE ANTIBODY

(76) Inventors: Hyun-Ju Doh, Dongdaemun-gu (KR); Doo-Sik Kim, Seodaemun-Gu (KR); Kwang-Hoe Chung, Seodaemun-Gu (KR)

( * ) Notice: Subject to any disclaimer, the term of this patent is extended or adjusted under 35 U.S.C. 154(b) by 791 days.

(21) Appl. No.: 12/428,321

(22) Filed: Apr. 22, 2009

(65) Prior Publication Data
US 2009/0298100 A1 Dec. 3, 2009

Related U.S. Application Data

(63) Continuation of application No. 11/997,247, filed as application No. PCT/KR2005/002491 on Jul. 29, 2005, now abandoned.

(51) Int. Cl.
| G01N 33/53 | (2006.01) |
| C12Q 1/00 | (2006.01) |
| A61K 39/395 | (2006.01) |
| C07K 16/18 | (2006.01) |
| G01N 33/86 | (2006.01) |

(52) U.S. Cl.
CPC .............. *C07K 16/18* (2013.01); *G01N 33/86* (2013.01); *C07K 2317/92* (2013.01); *G01N 2333/75* (2013.01)
USPC .................. 435/7.1; 435/4; 435/7.9; 435/13; 435/326; 435/337; 424/130.1; 424/139.1; 424/141.1; 424/158.1

(58) Field of Classification Search
CPC ..... A61K 39/395; A61K 38/08; A61K 38/16; C12Q 1/00; C12Q 1/28; G01N 33/52; G01N 33/536
USPC .......... 424/130.1, 139.1, 141.1, 158.1; 435/4, 435/7.1, 7.9, 13, 326, 337
See application file for complete search history.

(56) References Cited

U.S. PATENT DOCUMENTS

| 4,758,524 A | * | 7/1988 | Bundesen et al. | 435/7.92 |
| 4,879,217 A | * | 11/1989 | Petersen et al. | 435/7.31 |
| 5,206,140 A | | 4/1993 | Marder et al. | |
| 2012/0028370 A1 | * | 2/2012 | Nagai et al. | 436/501 |

OTHER PUBLICATIONS

Bach-Gansmo et al., "Degradation of Fibrinogen and Cross-Linked Fibrin by Human Neutrophil Elastase Generates D-Like Fragments Detected by ELISA but not Latex D-Dimer Test," Thrombosis Research (Nov. 1998), vol. 92 pp. 125-134.
Bennick et al., "D-Dimer Specific Monocorial Antibodies React with Fibrinogen Aggregates," Thrombosis Research (1996); vol. 82, No. 2, pp. 169-176.
Lawler et al., "Fibrin Fragment D-Dimer and Fibrinogen B beta Peptides inPlasma as Markers of Clot Lysis Dungn Thrombolytic Therapy in Acute Myocardial Infarction," Blood (Oct. 1990); vol. 76, No. 7, pp. 1341-1348.
Laroche et al., "Characterization of a Recombinant Single-Chain Molecule Comprising the Variable Domains f a Monoclonal Antibody Specific for Human Fibrin Fragment D-Dimer," J. Bio. Chem (Sep. 1991); vol. 266, No. 25, pp. 16343-16349.

* cited by examiner

*Primary Examiner* — Rodney P Swartz
(74) *Attorney, Agent, or Firm* — Fox Rothschild LLP; Shahnam Sharareh; Gerard P. Norton (57) ABSTRACT

Disclosed are a monoclonal antibody against human D-dimer produced in a mouse and high molecular weight cross-linked fibrin including a corresponding epitope, a cell line secreting the monoclonal antibody, and methods for producing the same. The anti-D-dimer monoclonal antibody of the present invention may be effectively used as a diagnotic agent for screening and detecting in-vivo D-dimer, and high molecular weight cross-linked fibrin and its derivatives containing the D-dimer since the monoclonal antibody specifically reacts with D-dimer, and cross-linked fibrin and its derivatives containing the D-dimer, which do not bind to human fibrinogen or fibrin.

23 Claims, 5 Drawing Sheets

|    | IgG1  | IgG2a | IgG2b | IgG3  | IgM   | IgA   | kapa  | Lamda |
|----|-------|-------|-------|-------|-------|-------|-------|-------|
| B1 | 0.605 | 0.082 | 0.083 | 0.076 | 0.092 | 0.075 | 0.712 | 0.081 |
| B2 | 0.532 | 0.081 | 0.081 | 0.086 | 0.086 | 0.076 | 0.637 | 0.082 |
| B3 | 0.421 | 0.081 | 0.083 | 0.080 | 0.095 | 0.075 | 0.534 | 0.086 |
| B4 | 0.648 | 0.095 | 0.082 | 0.082 | 0.096 | 0.086 | 0.703 | 0.091 |
| B5 | 0.682 | 0.097 | 0.088 | 0.021 | 0.093 | 0.085 | 0.614 | 0.090 |

Beta chain
```
120         130         140         150         160
 |           |           |           |           |
LKDLWQKRQK QVKDNENVVN EYSSELEKHQ LYIDETVNSN IPTNLRVLRS (SEQ ID NO: 3)

(SEQ ID NO: 4) DNENVVN EYSSELEKHQ LYIDETVNSN IPTNLRVLRS 38kDa (SEQ ID NO: 5) SSELEKHQ LYIDETVNSN IPTNLRVLRS 37kDa
```
DNENVVNEY: A epitope region to which B4 monoclonal antibody binds
(SEQ ID NO: 1)

FIG. 8

```
Column:  3B6/22  B4         3B6/22          B4
Plasma:   #4     #4    s   #1   2   3    1   2   3
```

← crosslinked
← Gamma-Gamma Chains

FIG. 9

| No. | B4/C3 | | Commercial kit(STAGO) | |
|---|---|---|---|---|
| | −Plasmin | +Plasmin | −Plasmin | +Plasmin |
| 1* | 3.44 | 3.05 | 0.85* | 2.89* |
| 2* | 2.42 | 2.51 | 0.51* | 1.56* |
| 3* | 3.46 | 3.14 | 1.61* | 3.61* |
| 4 | 1.87 | 1.9 | 1.76 | 2.06 |
| 5 | 2.24 | 2.42 | 2.56 | 2.67 |

MONOCLONAL ANTIBODY AGAINST D-DIMER AND DIAGNOSIS AGENT FOR DETECTING D-DIMER, CROSSLINKED FIBRIN AND ITS DERIVATIVES CONTAINING D-DIMER BY USING THE ANTIBODY

CROSS-REFERENCE TO RELATED APPLICATIONS

This application is a continuation filing of U.S. patent application Ser. No. 11/997,247 filed Jan. 29, 2008, now abandoned, which is a national phase filing of International patent application serial No. PCT/KR2005/002491, filed on Jul. 29, 2005, both of which are incorporated herein by reference.

TECHNICAL FIELD

The present invention relates to a monoclonal antibody against a high-molecular cross-linked fibrin including D-dimer and its corresponding epitope produced in a mouse, and a diagnosis agent for detecting D-dimer and cross-linked fibrin or its derivatives containing D-dimer by using the antibody.

More particularly, the present invention relates to a monoclonal antibody capable of being effectively used as a diagnosis agent for quantifying D-dimer and cross-linked fibrin or its derivatives containing D-dimer since the monoclonal antibody specifically reacts to human D-dimer and is manufactured with a high activity, wherein the monoclonal antibody is derived from a mouse and specifically binds to an amino acid sequence composed of amino acids 134 to 142 from an N terminus of a D domain beta-chain, or amino acids 134 to 142 from the N terminus of the D domain beta-chain and amino acids 124 to 214 of an alpha-chain, and a diagnosis agent for detecting D-dimer and cross-linked fibrin or its derivatives containing D-dimer by using the antibody.

BACKGROUND

Blood is regulated by two mechanisms: coagulation and fibrinolysis. The former is a mechanism for forming a thrombus and the latter is a mechanism for dissolving the thrombus. A fibrin is a major component constituting a thrombus and digests into several fibrin degradation products (FDP) through fibrinolysis. The formation and dissolution of fibrin substantially occur at the same times, and D-dimer is an important marker among the FDP produced in fibrin dissolution process. D-dimer is a final degradation product produced when an insoluble fibrin, in which gamma chains are cross-linked to each other by a factor XIII, is degraded by plasmin. It was known that FDP and D-dimer are detected at a higher concentration in plasma of patients suffering from various diseases such as pulmonary embolism, deep vein thrombosis, tumor surgery, disseminated intravascular coagulation, myocardial infarction, trauma, cancer, kidney and liver function impairment than in healthy humans. In particular, FDP and D-dimer have been the most used markers for diagnosing pulmonary embolism and deep vein thrombosis. Because pulmonary embolism and deep vein thrombosis do not have any distinct symptoms showing that the patients may develop pulmonary embolism and deep vein thrombosis, which eventually may lead to death. Also, only less than 20% of these patients were presented as a real positive through the medical examinations such as pulmonary angiography or venous ultrasonography which is widely practiced method for diagnosing these diseases until now. After introducing D-dimer as a diagnostic marker, up to 40% of the patients who are suspected of having thrombotic diseases can be easily diagnosed as a real patient without undergoing an extensive medical examination. There are many diagnostic agents for detecting a D-dimer such as SimpliRED kit (AGEN), an Asserchrom D-Di kit and an STA-Liatesr D-Di kit using an automation system (Diagnostica Stago), a VIDAS kit (BioMerieux SA, France), etc., but most of the diagnostic agents have common problems of low specificity. Also, test results are significantly different among the diagnosis agents since the different monoclonal antibodies; which adopted in each of the said diagnosis agents recognize different cross-linked fibrin degradation products, for instance, preferential binding of low molecular weight fibrin degradation product or of high molecular fibrin products. Actually, D-dimer level in patient's plasma is affected by various factors such as inflammatory diseases, age of patients, pregnancy, administration of an anti-coagulant, etc. in addition to the thrombosis. In particular, an erroneous diagnosis may be made in some test kits using a diagnostic agent specific to low-molecular weight fibrin degradation products since fibrin derivatives in plasma are present as a partially degraded form of cross-linked fibrin rather than a fully digested D-dimer form, especially in the case of the patients suffering from disseminated intravascular coagulation (DIC) syndrome for a long time and being subject to an anti-coagulation treatment (see Abraham Konberg, Blood 1992, vol 80, No 3, 709-717).

SUMMARY OF THE INVENTION

The monoclonal antibody produced in the present invention does not react to fibrinogen of normal human plasma, but specifically reacts to D-dimer produced in degradation of the cross-linked fibrin by plasmin, and cross-linked fibrin or its derivatives containing D-dimer. An ELISA diagnostic method using the monoclonal antibody produced in the present invention had excellent quantitative results than other diagnostic reagents in the test of plasma.

In the present invention, D-dimer-specific monoclonal antibodies were produced from hybridoma cell and purified from the cell culture supernatant, and then applied to the quantification of D-dimer or cross-linked fibrin or its derivatives containing D-dimer in the human body fluids through method of ELISA, LIA, etc.

Accordingly, the present invention is designed to solve the problems of the prior art, and therefore it is an object of the present invention to provide a murine monoclonal antibody capable of being effectively used as a diagnosis agent for screening and detecting D-dimer and cross-linked fibrin or its derivatives containing D-dimer since the monoclonal antibodies produced are highly reactive to D-dimer.

In order to accomplish the above object, the present invention provides a monoclonal antibody that specifically reacts to D-dimer and cross-linked fibrin or its derivatives containing D-dimer, wherein D-dimer is produced by converting human fibrinogen into fibrin using an enzyme thrombin, followed by digesting with plasmin. The monoclonal antibody of the present invention recognizes D-dimer and cross-linked fibrin or its derivatives containing D-dimer at the same time. D-dimer is produced by completely degrading cross-linked fibrin by plasmin. When an antibody reacts with only low-molecular weight fibrin degradation product, the high molecular weight fibrin degradation product may not be recognized by same antibody. Therefore, the concentration in the samples in which cross-linked fibrin is not degraded or partially degraded may be measured as much lower than their actual level. Thus, it is the most preferred to measure D-dimer level in plasma that the monoclonal antibodies used in D-dimer test recognize the cross-linked fibrin degradation products as well as D-dimer, but does not react with fibrinogen or its derivatives.

The antibody of the present invention preferably reacts to a site including an N-terminal amino acid sequence 134 to 142 of a beta-chain set forth in SEQ ID NO: 1, or a site including an N-terminal amino acid sequence 124 to 214 of an alpha-chain set forth in SEQ ID NO: 2.

Also, the present invention provides for diagnostic agents for detecting D-dimer and cross-linked fibrin products, including: a primary antibody that is a monoclonal antibody specifically reacting to D-dimer, or cross-linked fibrin or its derivatives containing D-dimer; and a secondary antibody conjugated with a marker; wherein the monoclonal antibody produced as a secondary antibody binds to the resulting primary antibody and D-dimer complex; and a substrate material for inducing color development by reacting to the marker.

According to the present invention, the marker is preferably selected from the group consisting of horseradish peroxidase (HRP) alkaline phosphatase. The substrate preferably includes at least one coupler selected from the group consisting of o-phenylenediamine and hydrogen peroxide.

BRIEF DESCRIPTION OF THE DRAWINGS

These and other features, aspects, and advantages of preferred embodiments of the present invention will be more fully described in the following detailed description, and accompanying drawings. In the drawings:

FIG. 1 is a diagram showing a photograph obtained by separating and purifying D-dimer. In FIG. 1, Lane 1 represents a soluble fibrin, Lane 2 represents α, β and γ chains of fibrinogen, Lane 3 represents a protein size marker (Molecular weight: 250, 150, 100, 75, 50, 37, 25, 15, 10 kDa), Lane 4 represents a, 13 and y chains of the separated and purified D-dimer, and Lane 5 represents an insoluble fibrin.

FIG. 6 is a photograph showing determination of an epitope recognized by the monoclonal antibody.

FIG. 8 is a diagram showing an SDS-electrophoretic result that the patient plasmas exhibiting different results in the ELISA method of the present invention and the commercially available diagnosis agent are passed through a column having each of the corresponding antibodies fixed therein, and then the resultant eluents are analyzed in an SDS-electrophoresis gel. Lanes #1, 2 and 3 represent the patient plasmas exhibiting the different results in the ELISA method, respectively, and Lane #4 represents the column eluents of the patient plasmas exhibiting the same results. In FIG. 8, "s" represents a protein size marker (Molecular weight: 100, 75, 50, 37, 25 kDa), and Arrows represent cross-linked gamma-gamma chains.

DETAILED DESCRIPTION OF THE INVENTION

Hereinafter, preferred embodiments of the present invention will be described in detail with reference to the accompanying drawings.

The present invention provides a fusion cell line that secrets anti-D-dimer monoclonal antibody, the fusion cell line being obtained by producing D-dimer from human fibrinogen, purifying D-dimer and immunizing a mouse with D-dimer.

A purity of D-dimer protein purified according to the method as described above was determined with the SDS-PAGE.

The fusion cell line producing the monoclonal antibody was prepared by immunizing mouse with D-dimer protein and fusing spleen cells from the immunized mouse with a mouse myeloma cell line. To select a positive clone of the fusion cell line producing the monoclonal antibody of the present invention, an enzyme-linked immunoassay (ELISA) was carried out on the purified D-dimer coated plate for screening, and a limiting dilution was carried out to separate a monoclonal antibody from the selected positive clone of high sensitivity. Finally, the monoclonal antibodies proven to have an anti-D-dimer specificity were named B2, C3, B4 and C5, respectively. The monoclonal antibodies of the present invention produced from the fusion cell line are IgG1-type kappa light chains and have a high specificity to a human D-dimer. Also, the monoclonal antibodies do not exhibit any cross-reactivity to structurally similar fibrinogen and its derivatives. It was found that an antigen recognition region of the monoclonal antibody B4, which is determined by western-blotting to the fragments of the purified D-dimer protein degraded by trypsin, chymotrypsin and CNBr, is composed of sites including N-terminal amino acid sequence 134 to 142 of a beta chain and N-terminal amino acid sequence 124 to 214 of the alpha chain. It was found from the experimental fact that the protein including the N-terminal amino acid sequence 134 to 142 of a beta chain is recognized by the monoclonal antibody B4, while the protein including the N-terminal amino acid sequence 134 to 431 of the beta-chain is not recognized by the monoclonal antibody B4.

Also, a protein encoded by the N-terminal amino acid sequence 124 to 214 of the alpha chain is weakly recognized by the monoclonal antibody B4 in comparison with the total D-dimer protein because the alpha chain and the beta chain are separated far from each other. Therefore, it was confirmed that the monoclonal antibody B4 recognizes a certain region of the unique string structure consist of twisting alpha, beta and gamma chain (see Brown J. H., Proc. Natl. Acad. Sci. USA 2000 97: 85-90; Evers S. J., Biochemistry 1999 38(10): 2941-2946).

Also, the present invention provides a diagnostic agent for screening and detecting D-dimer in plasma and cross-linked fibrin or its derivatives containing D-dimer, using the anti-D-dimer monoclonal antibody produced as described above.

The diagnostic agents of the present invention are composed of the anti-D-dimer monoclonal antibody as a primary antibody; a D-dimer monoclonal antibody produced as a secondary antibody by conjugating a marker such as horseradish peroxidase with the said antibody; and a substrate solution including a material for inducing color development by reacting with the marker.

D-dimer monoclonal antibody used as a secondary antibody conjugate has a marker conjugated thereto. At this time, horseradish peroxidase (HRP), alkaline phosphatase, and other suitable markers may be used as markers. The presence of the D-dimer antigen may be determined by the binding of the antigen present in the sample to a primary antibody immobilized on solid surface. Secondary antibody conjugate then forms a sandwich complex.

The substrate solution for inducing color development by reacting with the marker includes a buffer and a coupler such as o-phenylenediamine, hydrogen peroxide solution, etc. The substrate solution may develop colors by reaction of the marker conjugated to the monoclonal antibody, and therefore the presence and an amount of the antigen may be determined by measuring a level of the color development.

Ultimately, the concentration of D-dimer or high molecular weight cross-linked fibrin degradation product in tissue sections, whole blood, plasma, cells or like may be quantitatively analyzed with the diagnosis agents on the crude samples themselves or by using ELISA, western blotting, immunoprecipitation or like.

Hereinafter, preferred embodiments of the present invention will be described in detail.

However, it should be understood that the description proposed herein is just a preferable example for the purpose of illustrations only, not intended to limit the scope of the invention.

Example 1

Preparation and Purification of Human D-Dimer Protein

Figure 1:
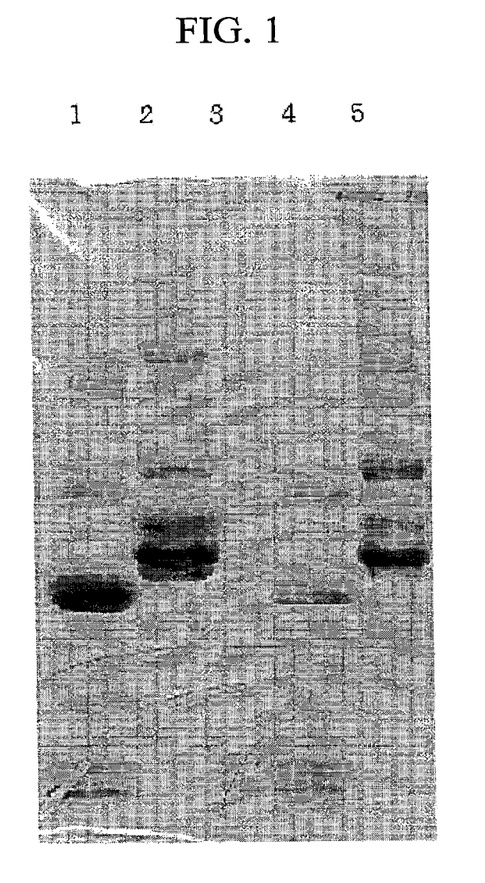

As an antigen D-dimer was obtained by converting human fibrinogen into fibrin using an enzyme thrombin, cutting fibrin with an enzyme plasmin and purifying the resultant fragments of fibrin. That is to say, a reaction buffer was prepared by dissolving 50 mM Tris-HCl (p 117.5), 0.1 M NaCl and 16 mM $CaCl_2$ and adding 5% human plasma as a source of Factor XIII. Bovine thrombin was added at an amount of 500 unit per 1 g of fibrinogen and reacted at room temperature for 16 hours to form a fibrin mass, and then fibrin mass was immersed in 2% acetic acid solution for 16 hours to remove un-cross-linked fibrin. Fibrin mass was thoroughly washed with distilled water, frozen with liquid nitrogen, milled, and then put into a reaction buffer. 1 unit of urokinase was added to 1 unit of plasminogen, and the resultant mixture was reacted at 37° C. for 30 minutes to form an active plasmin. Then, 1 unit of plasmin per 500 mg of fibrin was added, put into a reaction buffer, and reacted at 37° C. for 72 hours while adding 1 unit of the active plasmin every 24 hours. After 72-hour reaction, 400 unit of aprotinin was added to stop the reaction. It was confirmed that D-dimer was produced since a cross-linked gamma chain was observed near a band of 80 kDa in SDS-PAGE (FIG. 1).

Gel permeation chromatography was used to purify D-dimer from the produced fibrin degradation products. At this time, the buffer used is 50 mM phosphate solution (pH7.5) containing 6M urea, and the gel permeation chromatography was carried out according to the method proposed by Olexa S A, and Budzynski A Z, et al. (Proc Natl Acad Sci USA., 1980, March 77(3): 1374-1378) was confirmed that D-dimer was separated and purified using SDS-electrophoresis and ELISA, and D-dimer having a purity of at least 90 was used as an antigen (FIG. 1).

Example 2

Preparation of Fusion Cell Line Producing Monoclonal Antibody Specific to D-Dimer In order to prepare a fusion cell line that produces a monoclonal antibody, an 8-week-old experimental female mouse (BALB/c mouse) was immunized, as follows. Firstly, 50 μl of D-dimer protein, expressed and purified in Example 1, was mixed at the same volume with 150 μl of complete Freund's adjuvant (Sigma) to prepare an emulsifying solution, and then the emulsifying solution was peritoneally administered to a BALB/c mouse. After the first administration, D-dimer protein was emulsified in incomplete Freund's adjuvant (Sigma) at the same amount, and then the resultant emulsifying solution was peritoneally injected to a BALB/c mouse upon the first and second administrations every 10 days, and 20 μg of D-dimer protein was injected upon the third and fourth peritoneal administrations to stimulate a specific immune reaction. Finally, only 20 μg of D-dimer protein was peritoneally administered to a BALB/c mouse at 3 days before a fusion cell line was prepared completely. In order to prepare a fusion cell line, a spleen cell was taken from the immunized mouse, and mixed with mouse myeloma cell line Sp2/0-Ag14(ATCC, U.S.) at a cell ratio of 2:1. Then, the cell mixture was centrifuged to remove a supernatant, and then 1 ml of PEG-1500 (polyethylene glycol-1500, Boehringer Mannheim) was added and thoroughly mixed for 1 minute using a plastic Pasteur pipette, and 15 ml of a serum-free DMEM culture solution (Gibco) was added dropwise over 10 minutes and thoroughly mixed, and then the same volume of DMEM medium containing 20% fetal bovine serum was added and kept at 37° C. for 30 minutes. The cell suspension was centrifuged, and the precipitated cell pellet was added to a DMEM medium containing 20% fetal bovine serum again, and the resultant mixture was divided at an amount of 100 μl into a 96-well plate, and incubated overnight at 37° C. under a 5% $CO_2$ atmosphere condition. After 1-day incubation, a 2× HAT medium (Sigma) was added at an amount 100 μl to each plate and incubated to form colonies. After the colonies were then formed, an enzyme-linked immunoassay (ELISA) was carried out using the purified D-dimer to select positive colonies, but to exclude the positive colonies against fibrinogen and its derivatives.

In particular, the purified D-dimer and fibrinogen and its derivatives, respectively, were thoroughly mixed in a coating buffer (0.1M Na-carbonate, pH 9.5), added at an amount of 1 μg to each 96-well ELISA plate (Maxisorp, Nunc), and then reacted overnight at 4° C. In the next day, a blocking buffer (1% bovine serum albumin/PBS) was added and kept at room temperature for 2 hours. Then, the solution was removed off, each of the wells was washed with a washing solution, a culture solution of the fusion cell line was added at an amount of 100 μl to each well and reacted at 37° C. for 1 hour. Then, an excessive amount of the non-reacted antibody was removed off, goat-derived anti-mouse IgG antibody (KPL) to which horseradish peroxidase (HRP) binds, o-phenylenediamine (Sigma) which is a substrate of HRP, and hydrogen peroxide solution ($H_2O_2$) was sequentially added to confirm whether or not the specifically bound antibody is present in the culture solution. As a result, the hybridoma clones, which exhibit the reactivity to D-dimer protein but do not react to fibrinogen and its derivatives, were selected as positive clones that secret the antibody against D-dimer.

A limiting dilution was carried out to separate a monoclonal clone from the positive clones selected in the above-mentioned procedure.

For this purpose, all of the cell lines present in the 96-well plate were taken and suspended to count the cells. Then, the cells were dividedly added at an amount of 0.3 cells per a well of the 96-well plate, and then the 96-well plates were sequentially prepared at an amount of 1 cell, 10 cells and more per a well, respectively. At this time, the clones, grown in the plate including the smallest amount of the cells, were selected and grown again, and the above-mentioned procedure was repeated, if necessary. Finally, the clone grown in the most diluted density of the plate was considered to be a monoclonal clone.

By carrying out the procedure, the monoclonal antibodies, finally proven to have an anti-D-dimer specificity, were named B2, C3, B4 and C5, respectively.

Example 3

Characterization of Prepared Monoclonal Antibodies B2-05

Figure 2:
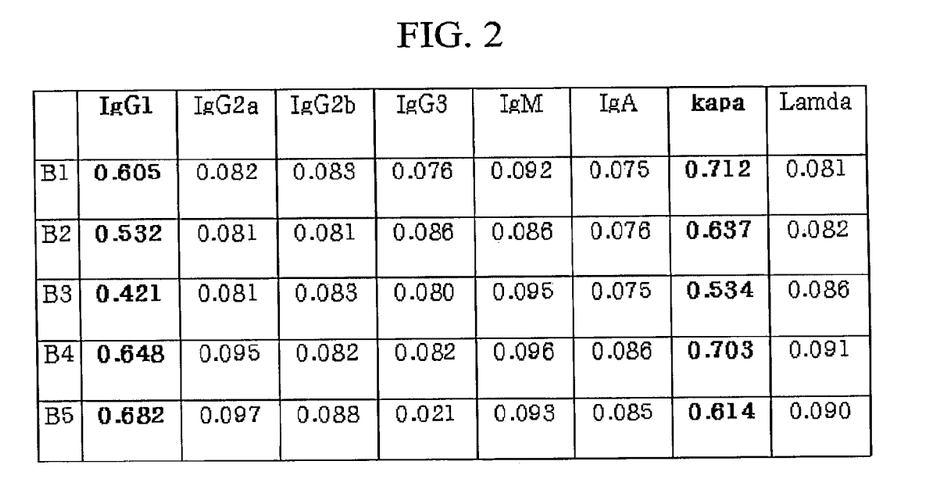
FIG. 2 is a table illustrating isotype of the monoclonal antibodies.
Figure 3:
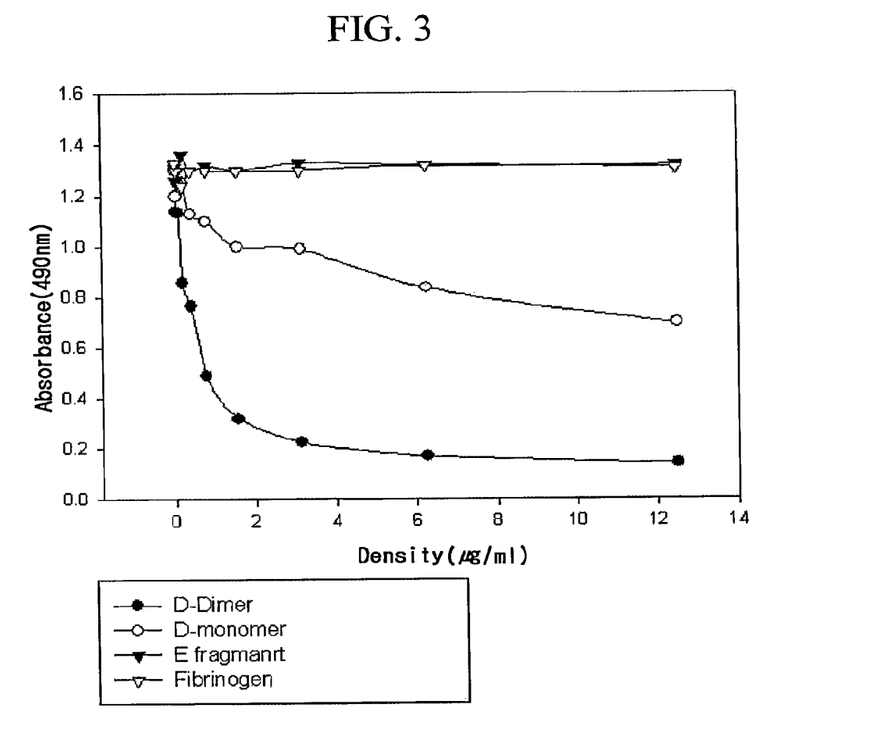
FIG. 3 is a diagram showing cross-reactivity of a monoclonal antibody B4 on a D-dimer.

In order to determine immunoglobulin antibody types of the monoclonal antibodies, a kit (Pierce) for determining mouse immunoglobulin type was used. Firstly, wells of ELISA plate were coated with an antigen, the purified monoclonal antibodies were added thereto, and rabbit-derived anti-mouse immunoglobulin antibodies, respectively, specific to the mouse immunoglobulin types were added, and then goat-derived anti-rabbit immunoglobulin antibodies to which horseradish peroxidase (HRP) binds were added to screen whether or not positive results are found in the monoclonal antibodies. As a result, it was confirmed that all the monoclonal antibodies are kappa light chains of IgG1, as shown in FIG. 2.

Example 4

Test of Antigen Specificity to B4 a. Determination of Antigen Specificity to Monoclonal Antibody B4

Figure 4:
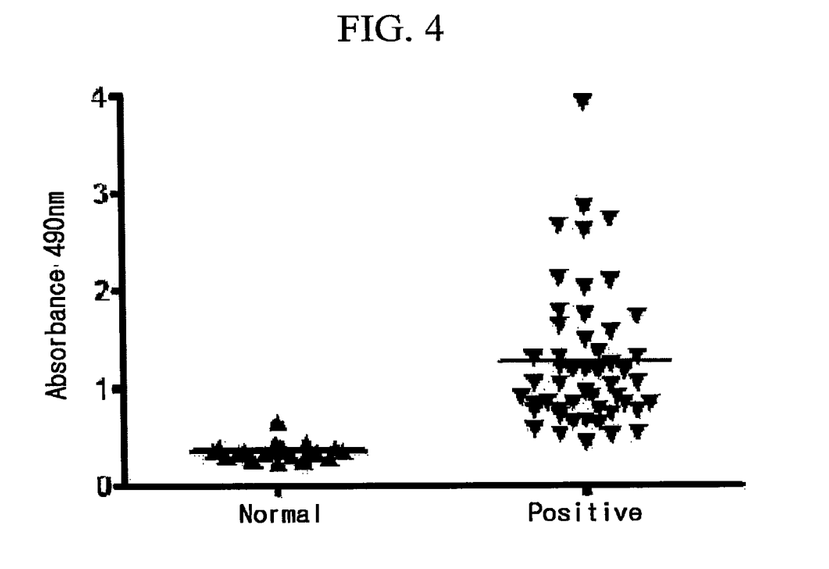
FIG. 4 is a diagram showing plasma test results of a normal human and a patient having a high level of D-dimer using monoclonal antibodies B4 and B2.

In order to determine antigen specificity to monoclonal antibody 134 using an enzyme-linked immunoassay, a competitive inhibition enzyme-linked immunosorbent assay (ELISA) was carried out. For this purpose, the human D-dimer prepared in Example 1 was thoroughly mixed in a coating buffer (0.1M Na-carbonate, pH 9.5), and the mixture was added at an amount of 1 μg to each well of a 96-well ELISA plate(Maxisorp, Nunc), and then reacted overnight at 4° C. The antigen coating solution was removed off, and a blocking buffer (1% bovine serum albumin/PBS) was added and kept at a room temperature for 2 hours. Then, the solution was removed off, and each 10 of the wells was washed with a PBST (prepared by adding 0.1% Tween 20 to phosphate-buffered saline) buffer. In order to confirm specificity of an antigen that reacts to the monoclonal antibody B4, 25 μg/ml of each of D-dimer, D monomer, E domain and fibrinogen was firstly reacted to monoclonal antibody B4 to which horseradish peroxidase (HRP) binds at 37° C. for 1 hours, respectively, and then the reaction solutions were added to the plates coated with D-dimer. In addition, the reaction solutions was further reacted at 37° C. for 1 hour, and removed off, and the plate was washed, and o-phenylenediamine (Sigma) which is a substrate of HRP, and hydrogen peroxide solution ($H_2O_2$) were sequentially added to confirm whether or not the specifically bound antibody is present in the culture solution. As a result, it was seen that the monoclonal antibody B4 has a high dissociation constant of $9.8 \times 10^{-10}$ M, and it was also seen that the monoclonal antibody B4 has a low reactivity of $5 \times 10^{-6}$ M to the D monomer and is specific to D-dimer exhibiting no cross reactivity to fibrinogen fragments such as fibrinogen, E domain (FIG. 4).

b. Determination of Antigen Specificity to Monoclonal Antibody Using Western Blotting In order to determine an antigen specificity to the monoclonal antibodies, D-dimer, D monomer, E domain and fibrinogen were electrophoresed on a SDS-PAGE gel, and the resultant gel was then transferred to 0.45 μm of a nitrocellulose membrane (Bio-rad) in a Iris-glycin-methanol buffer and blotted. In order to remove non-specific reaction products, the nitrocellulose membrane was blocked with 5% nonfat dry milk at room temperature for 2 hours, and then the monoclonal antibody B4 specific to D-dimer was diluted to a suitable density and reacted for 1 hour. Then, the nitrocellulose membrane was washed with a PBS buffer containing 1% Tween-20, and then an horseradish peroxidase (HRP) conjugated anti-mouse IgG antibody (Sigma) was diluted at a volumetric ratio of 1:2500 and reacted for 1 hour, and the reagents were removed off by washing the same volume of the PBS buffer, and developed with 4-chloro-1-naphthol and $H_2O_2$. As a result, it was found that the B4 reacts to only D-dimer.

Example 5

Identification of Fine Epitope to B4 a. Determination of Fine Epitope to B4

Figure 6:
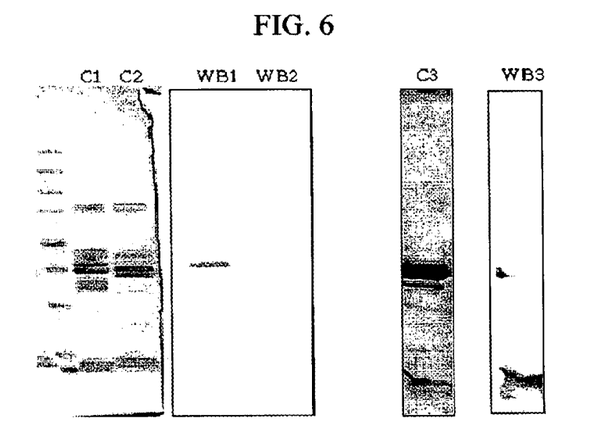
In FIG. 6, Leftmost lane represents a protein size marker (Molecular weight: 250, 150, 100, 75, 50, 37, 25, 15, 10 kDa), Lane CI represents trypsin-treated D-dimer fragments (Coomassie blue staining), Lane C2 represents chymotrypsin-treated D-dimer fragments (Coomassie blue staining), Lane WB1 represents trypsin-treated D-dimer fragments (Western blotting), and Lane WB2 represents chymotrypsin-treated D-dimer fragments (Western blotting).
Figure 7:
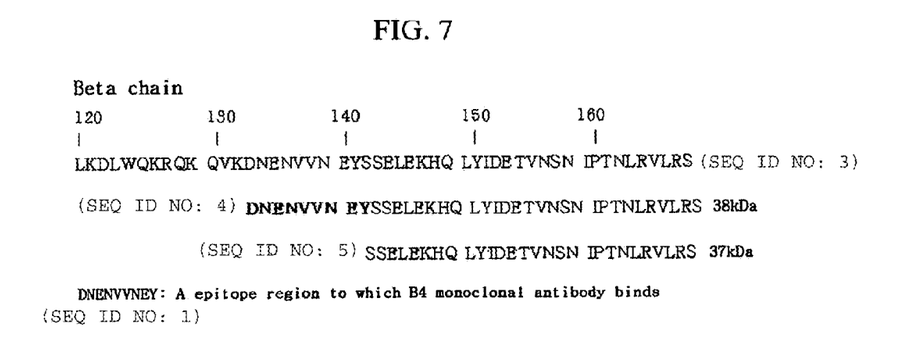
FIG. 7 is a diagram showing an epitope region of the monoclonal antibody B4 confirmed using an amino acid sequence analysis of 38 and 37 kDa fragments.

In order to determine a fine epitope to the monoclonal antibody B4 using D-dimer protein, D-dimer protein was degraded with various enzymes and a western blotting was carried out on the degradation products of D-dimer. The equivalent amount of D-dimer protein was degraded at a volumetric ratio of 1:10 to 1:100 with trypsin, chymotrypsin, pepsin and CNBr at 37 C for 30 minutes to 4 hours. Its degradation products were divided into two groups and electrophoresed in a non-reduced gel and a reduced gel, respectively. The resultant gels were transferred to nitrocellulose membranes, and then western blotting was carried out using the monoclonal antibody B4 in the same manner as described above in Example 4b. As a result, it was revealed that D-dimer protein and its fragments degraded by trypsin and chymotrypsin were recognized by the monoclonal antibody B4 in the non-reduced gel, but only the beta chain or the 38-Da fragment degraded by trypsin was recognized by the monoclonal antibody B4 in the reduced gel (C1 and WB1 in FIG. 6). Meanwhile it was revealed that the 37-kDa fragment degraded by chymotrypsin was not recognized (C2 and WB2 in FIG. 6). In order to determine from which site of the protein the reactivity difference is derived in the two fragments, an N-terminal amino acid sequence analysis and MS/MS analysis were carried out. As a result, it was found that C-terminuses of the two protein fragments were identical to each other, but their N-terminuses were different to each other, and therefore a peptide fragment consisting of 9 amino acid residues from the N-terminus of the beta chain, that is a B134-B142 fragment, was recognized by the monoclonal antibody B4, as shown in FIG. 7. Also, it was found that the 13-kDa fragment was recognized by the monoclonal antibody B4 even when the western blotting was carried out on the fragment degraded by the CNBr treatment (C3 and WB3 in FIG. 6), and a fine epitope of the monoclonal antibody B4 corresponds to the protein fragment consisting of amino acid sequences 124 to 214 of the alpha chain when the fragment was analyzed using the MS/MS analysis. It was found that the two sites of the protein fragments are portions of a string structure in which alpha, beta and gamma chains are twisted to each other, which are widely known as regions that are hidden in fibrinogen but newly exposed when fibrinogen is cut by plasmin after its crosslinking reaction (see Brown J. H., Proc. Natl. Acad. Sci. USA 2000 97: 85-90; Evers S. J., Biochemistry 1999 38(10): 2941-2946).

Example 6

Determination of D-Dimer Density in Human Plasma Using C3/B4

A density of D-dimer or fibrin degradation products containing D-dimer might be measured using the monoclonal antibody B4 specific to D-dimer. The measurement was carried out using a double antibody sandwich ELISA. A monoclonal antibody C3 was thoroughly mixed in a coating buffer (0.1M Na-carbonate, pH 9.5), and the resultant mixture was added at an amount of 1 μg to each of the 96-well ELISA plate (Maxisorp, Nunc), and then reacted overnight at 4° C. A non-coated antibody was removed off, and a blocking buffer (1% bovine serum albumin/PBS) was added and reacted at a room temperature for 2 hours, and then each of the wells was washed with a PBST (prepare by adding 0.1% Tween 20 to phosphate-buffered saline) buffer. Human plasma was diluted 20 times with the 1% bovine serum albumin/PBS buffer, added at an amount of 100 μl to each well, and then reacted at 37° C. for 1 hour. After the solution was reacted at 37° C. for 1 hour, the solution was removed off, and then each of the wells was washed 4 times with a washing solution. Then, D-dimer-specific monoclonal antibody B4 to which horseradish peroxidase (HRP) binds was diluted at 1:2000 with a 1% bovine serum albumin/PBS buffer, added at an amount of 100 μl to each well, and then further reacted at 37° C. for 1 hour. O-phenylenediamine (Sigma) which is a substrate of I-IRP, and hydrogen peroxide solution ($H_2O_2$) were sequentially added to confirm whether or not the specifically bound antibody is present in the culture solution. As a result, absorbance of the culture solution was quantitatively increased according to the density of D-dimer in plasma of the patients, and therefore a patient group was distinguishable from a normal group (FIG. 4).

Example 7

Comparison Between Conventional Diagnosis Agent and ELISA Diagnosis Prepared Using C3/B4 a. Comparison Test Between DIC-Suspected Patient Group and Normal Group

Figure 5:
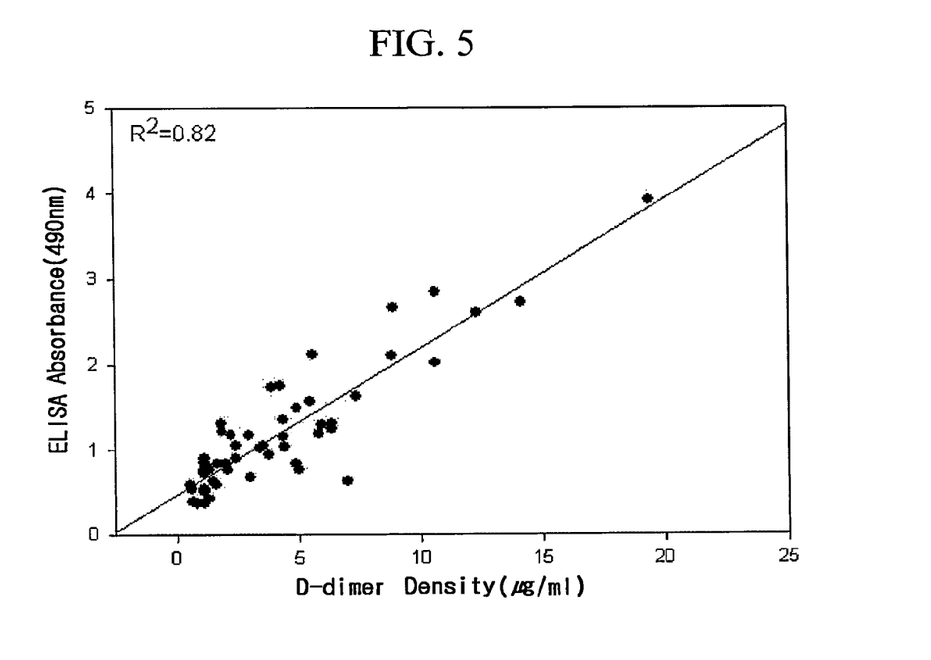
FIG. 5 is a diagram showing that a level of D-dimer in plasma from thrombosis-suspected patients is measured by an ELISA method using monoclonal antibodies C3/B4.
Figure 8:
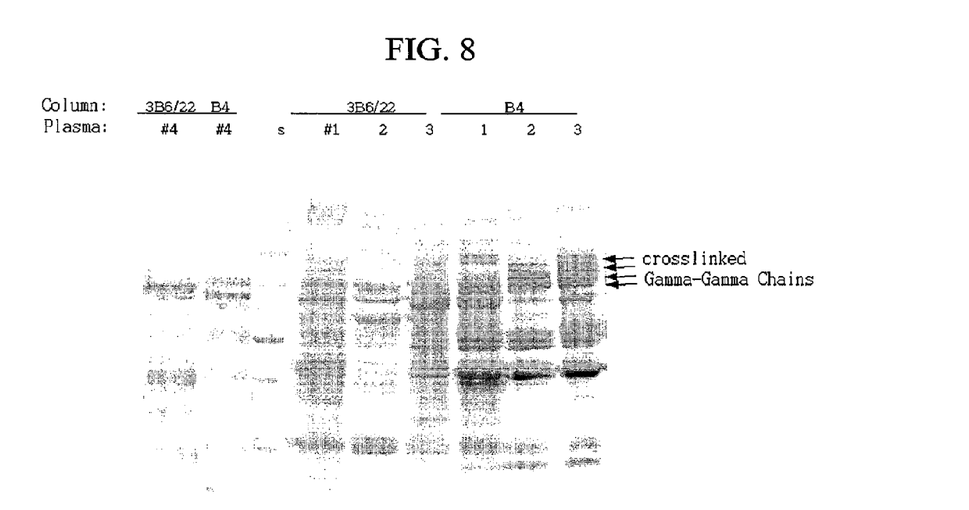

A density of D-dimer in plasma of DIC-suspected patient group and a normal group was measured in the same manner as described above in Example 6, and a commercially available diagnosis agent (AGEN) was also tested according to the procedure as described in a manufacturer's manual, and then a linearity was plotted by comparing absorbances which are the test results of the patient samples (FIG. 5). As a result, it was revealed that the two measurement methods are tested using the same material, for example D-dimer, and also have a high correlation. However, the ELISA results of the present invention were measured at a very higher level than that of the commercially available diagnosis agent in the case of some DIC-suspected patients, but it was considered that the diagnostic results of the present invention is more reliable since all of the patient samples were obtained from patients who were proven to be acute DIC patients on the basis of partial thromboplastin time (PTT) delayed syndrome, a reduced amount of platelet and fibrinogen, a positive reaction of D-dimer, etc.

b. Difference Analysis from Commercial Diagnosis Agent Using Monoclonal Antibodies DD3B6/22 and B4 Column This experiment was carried out in the case of the patients exhibiting the relatively high difference between the commercially available diagnosis agent and the ELISA method, as described above in Example 7. The monoclonal antibodies DD3B6/22 and B4 used for the commercially available diagnosis reagent were fixed to a sepharose resin, activated with N-hydroxysuccinimide (NHS), according to the van Sommeren's method to prepare columns, respectively. The three plasma (samples 1, 2 and 3 in FIG. 8 and FIG. 9) exhibiting the different results in Example 6 were passed through the column prepared thus, and then SDS-PAGE was carried out on the eluent fragments to confirm band patterns of D-dimer respectively recognized by the monoclonal antibodies. As shown in FIG. 8, bands of the cross-linked gamma-gamma-chains and the beta chains were clearly observed in the sample fragments 1, 2 and 3 eluted from the B4 column, while these bands were not present or rarely observed in the sample fragments eluted from the DD3B6/22 column. The presence of the gamma-gamma chain having a molecular weight of at least 80 kDa means that the cross-linked fibrin is not degraded completely. Even in the case of the plasma sample 4 having the nearly same ELISA results in the above-mentioned two methods, band patterns of the sample fragments eluted from the two columns were confirmed in the same manner as described above. In this case, the similar band patterns were observed in the two columns. From these results, it was seen that, since fibrin degradation products were not present as the completely degraded D-dimer but the cross-linked fibrin or its derivatives in plasma of some patients, an amount of D-dimer was detected at a lower level than that of the actual D-dimer in the case of the DD3B6/22 that does not recognize the cross-linked fibrin or its derivatives, or in the case of the diagnostic agent using the DD3B6/22 (see Carl E. D., Thromb Haemost 2001 85:671-678).

c. ELISA Signal Change in Plasmin-Treated Plasma of DIC-Suspected Patient

Figure 9:
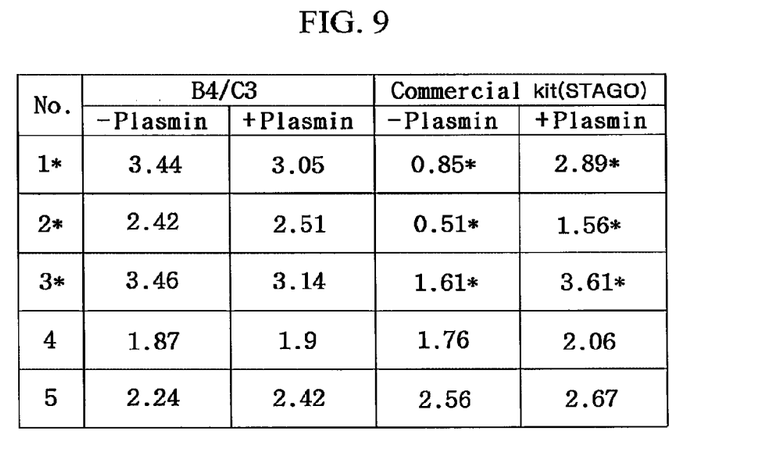
FIG. 9 is a table showing a profile that detection signals are increased when the undissolved cross-linked fibrin, which is present in the plasma from the disseminated intravascular coagulation (DIC)-suspected patients, is artificially degraded by adding plasmin.

The partially degraded cross-linked fibrin or its derivatives were artificially degraded by treating the patient plasma samples 1, 2, 3 and 4 with plasmin according to the same method as described in Example 1, and then a density of D-dimer in the plasma samples was measured again using the ELISA diagnosis agent. As shown in FIG. 9, it was revealed that ELISA signals were significantly increased when the plasmin-treated patient plasma samples 1, 2 and 3 were tested using the commercially available diagnosis agent, while ELISA signals were similar or reduced when the plasmin-treated patient plasma samples 1, 2 and 3 were tested using the C3/B4 ELISA method of the present invention. Accordingly, the ELISA diagnostic method of the present invention has a performance to detect D-dimer as well as the cross-linked fibrin and its derivatives, and therefore may be especially useful to diagnose a population having a large amount of the high molecular weight cross-linked fibrin in plasma, for example patients suffering from thrombosis for a long time, or patients who are subject to the early thrombus treatment.

d. Clinical Trial on Rapid Kit Prepared Using Monoclonal Antibodies C3/B4

A D-dimer Rapid kit was prepared according to a conventional method using the monoclonal antibodies (mAb) C3 and B4 of the present invention. As shown in FIG. 9, it was seen that the mAb of the present invention more specifically binds to the untreated high molecular weight (HMW) fibrin, compared to other commercially available kits. In addition, it was known the diagnosis kit (AGEN) more sensitively reacts to the HMW-fibrin and the diagnosis kit (Stago) more sensitively reacts to the LMW-fibrin (Dempfle C E, et al., Thromb Haemost 2001; 85: 671-8). In the present invention, D-dimer levels in the four clinical samples of the present invention were overestimated and reduced after the plasmin treatment, compared to the diagnosis kit (Stago). On the contrary, D-dimer levels were increased by the pre-treatment of the plasma samples with plasmin in the diagnosis kit (Stago). According to the Fibrin Assay Comparison Trial (FACT) study by Demple C E, et al. (Thromb haemost, 2001, 85: 671-8; and Thromb Haemost 2001, 86: 1204-9), and a report by Gaffney et al. [Gaffney P J, et al., Br J Haematol 1995; 90:187-94], it was found that Fibrin Degradation Products (FnDPs) produced under a flowing condition is mainly composed of HMW-derivatives rather than D-dimer fragments, and HMW-fibrin oligomers are major targets for analyzing D-dimer in the clinical samples. In this aspect, the mAb of the present invention may be used as a reliable and improved method capable of detecting low molecular weight (LMW) dimer as well as HMW-fibrin without any of their cross reactivity in the clinical trial.

INDUSTRIAL APPLICABILITY

As described above, the anti-D-dimer monoclonal antibody of the present invention may be more useful to diagnose DIC-suspected patients, compared to the conventional antibodies specific only to D-dimer, since the anti-D-dimer monoclonal antibody is a kappa light chain of an IgG1 type, and specifically reacts to a human D-dimer but does not exhibit a cross reactivity to the other structurally similar proteins, and also specifically reacts to a high molecular weight cross-linked fibrin containing a sugar epitope. The monoclonal antibody of the present invention may be effectively used as a diagnosis agent for screening and detecting D-dimer in tissues and blood vessels, and in particular useful to diagnose diseases such as disseminated intravascular coagulation (DIC), pulmonary embolism (PE), various thrombosis since the monoclonal antibody is manufactured with a high activity and specifically reacts to D-dimer.

What is claimed is:

1. A monoclonal antibody that binds to D-dimer and crosslinked fibrin, wherein the monoclonal antibody binds to a site comprising the amino acid sequence set forth in SEQ ID NO: 1.

2. A monoclonal antibody that binds to D-dimer and crosslinked fibrin, wherein the monoclonal antibody binds to a site comprising the amino acid sequence set forth in SEQ ID NO: 2.

3. A diagnostic construct for detecting D-dimer and crosslinked fibrin comprising:
   (a) a first monoclonal antibody that binds to D-dimer and crosslinked fibrin, wherein the monoclonal antibody binds to a site comprising the amino acid sequence set forth in SEQ ID NO: 1 and
   (b) a second monoclonal antibody that binds to D-dimer and crosslinked fibrin, wherein the second monoclonal antibody binds to a site comprising the amino acid sequence set forth in SEQ ID NO: 2 and said antibodies form a sandwich having a D-dimer or crosslinked fibrin molecule as a target analyte to be detected; and
   (c) an optional substrate including a material for inducing color development by reacting with a marker.

4. The diagnostic construct for detecting D-dimer and crosslinked fibrin according to claim 3, wherein the marker is colloidal gold sol, horseradish peroxidase (HRP) or alkaline phosphatase.

5. The diagnostic construct for detecting D-dimer and crosslinked fibrin according to claim 4, wherein the substrate further includes a coupler selected from the group consisting of O-phenylenediamine and hydrogen peroxide.

6. A kit for detecting D-dimer comprising a monoclonal antibody that binds to a site comprising the amino acid sequence set forth in SEQ ID NO: 1 or the amino acid sequence set forth in SEQ ID NO: 2.

7. The kit according to claim 6, wherein any one of said monoclonal antibodies are immobilized to a solid surface as a capture antibody and the other antibody is labeled with a detector probe wherein the detector probe is selected from a group consisting of metallic colored materials, non-metalic colored materials, chromogenic material, fluorochromic material, and other luminous material wherein the detector probe is suitable for visual or quantitative detection of D-dimer and is an aid for diagnosis of clinical symptoms associated with or resulting in the rise of the level of D-dimer in a patient's blood.

8. The monoclonal antibody according to claim 1, wherein the monoclonal antibody binds with a site on a beta-chain of the D-dimer and the crosslinked fibrin.

9. The monoclonal antibody according to claim 2 wherein the antibody binds with a site on the alpha-chain of D-dimer and crosslinked.

10. A diagnostic construct for detecting D-dimer and crosslinked fibrin, comprising:
    (a) a first monoclonal antibody as a primary antibody that binds with a site on a beta-chain of the D-dimer and the crosslinked fibrin;
    (b) a second monoclonal antibody as a secondary antibody that binds with a site on an alpha-chain of D-dimer and crosslinked fibrin; and
    (c) a substrate or detector probe including a material for inducing color development by reacting with a marker.

11. The diagnostic construct for detecting D-dimer and crosslinked fibrin according to claim 10, wherein the marker is horseradish peroxidase (HRP) or alkaline phosphatase.

12. The diagnostic construct for detecting D-dimer and crosslinked fibrin according to claim 10, wherein the substrate includes a coupler selected from the group consisting of o-phenylenediamine and hydrogen peroxide.

13. A kit for detecting a rise in D-dimer level in blood comprising a first monoclonal antibody that is immobilized on a solid surface as a capturing agent that binds to a site comprising the amino acid sequence set forth in SEQ ID NO: 1 and a second antibody that binds to a site comprising the amino acid sequence set forth in SEQ ID NO: 2, said antibodies are independently labeled with a detector probe, wherein the detector probe is selected from a group consisting of metallic colored materials, non-metalic colored materials, chromogenic material, fluorochromic material, and other luminous material wherein the detector probe is suitable for visual or quantitative detection of D-dimer.

14. A kit for detecting clinical symptoms of thrombosis and embolism comprising: at least one monoclonal antibody that is immobilized on a solid surface as a capturing agent that binds to a site comprising the amino acid sequence set forth in SEQ ID NO: 1 or in SEQ ID NO: 2, wherein the monoclonal antibody is used in a competitive assay or in sandwich immunoassay for the detection and quantitation of D-dimer and is an aid for diagnosing of clinical symptoms associated with or resulting in increased levels of D-dimer in a patient's blood.

15. A hybridoma that produces a monoclonal antibody or fragment thereof wherein the monoclonal antibody binds to a site comprising the amino acid sequence set forth in SEQ ID NO: 1 or 2.

16. A diagnostic method for detecting a rise in plasma concentration of D-dimer and crosslinked fibrin comprising:
    (a) applying a first monoclonal antibody that binds to a region of D-dimer or crosslinked fibrin molecule comprising an amino acid sequence set forth in SEQ ID NO: 1 to a sample obtained from a patient in need thereof,
    (b) applying a second monoclonal antibody that binds to a region of D-dimer or crosslinked fibrin molecule comprising amino acid sequence set forth in SEQ ID NO: 2 to said sample,
    (c) forming at least one immunocomplex between at least one of said antibodies and the D-dimer or crosslinked fibrin molecule as a target analyte,
    (d) quantitatively detecting the presence or absence of said target analyte using a detector probe which binds to the immunocomplex, wherein an increase in the quantitative detection of said probe signifies a rise in plasma concentration of the target analyte.

17. The method of claim 16, further comprising the step of reacting a marker enzyme to the detector probe to induce color development.

18. The method of claim 17, wherein the marker is horseradish peroxidase (HRP) or alkaline phosphatase.

19. The method of claim 16, wherein the rise in the plasma concentration of target analyte the presence of a pathological condition secondary to activated clotting factor.

20. The method of claim 16, wherein said detector probe is selected from a group consisting of metallic colored materials, non-metalic colored materials, chromogenic material, fluorochromic material.

21. The method of claim 16, further comprising the step of immobilizing the first monoclonal antibody on a solid surface.

22. The method of claim 16, further comprising the step of reacting the first monoclonal antibody with a plasma sample containing the D-dimer targeting analyte.

23. The method of claim 16, wherein said sample is a blood or a tissue sample.

* * * * *

SEQUENCE LISTING

```
<160> NUMBER OF SEQ ID NOS: 6

<210> SEQ ID NO 1
<211> LENGTH: 9
<212> TYPE: PRT
<213> ORGANISM: Homo sapiens

<400> SEQUENCE: 1

Asp Asn Glu Asn Val Val Asn Glu Tyr
1               5

<210> SEQ ID NO 2
<211> LENGTH: 91
<212> TYPE: PRT
<213> ORGANISM: Homo sapiens

<400> SEQUENCE: 2

Asp Asn Thr Tyr Asn Arg Val Ser Glu Asp Leu Arg Ser Arg Ile Glu
1               5                   10                  15

Val Leu Lys Arg Lys Val Ile Glu Lys Val Gln His Ile Gln Leu Leu
            20                  25                  30

Gln Lys Asn Val Arg Ala Gln Leu Val Asp Met Lys Arg Leu Glu Val
        35                  40                  45

Asp Ile Asp Ile Lys Ile Arg Ser Cys Arg Gly Ser Cys Ser Arg Ala
    50                  55                  60

Leu Ala Arg Glu Val Asp Leu Lys Asp Tyr Glu Asp Gln Gln Lys Gln
65                  70                  75                  80

Leu Glu Gln Val Ile Ala Lys Asp Leu Leu Pro
                85                  90

<210> SEQ ID NO 3
<211> LENGTH: 50
<212> TYPE: PRT
<213> ORGANISM: homo sapiens

<400> SEQUENCE: 3
```

Leu Lys Asp Leu Trp Gln Lys Arg Gln Lys Gln Val Lys Asp Asn Glu
1               5                   10                  15

Asn Val Val Asn Glu Tyr Ser Ser Glu Leu Glu Lys His Gln Leu Tyr
                20                  25                  30

Ile Asp Glu Thr Val Asn Ser Asn Ile Pro Thr Asn Leu Arg Val Leu
            35                  40                  45

Arg Ser
    50

<210> SEQ ID NO 4
<211> LENGTH: 50
<212> TYPE: PRT
<213> ORGANISM: Homo sapiens

<400> SEQUENCE: 4

Leu Lys Asp Leu Trp Gln Lys Arg Gln Lys Gln Val Lys Asp Asn Glu
1               5                   10                  15

Asn Val Val Asn Glu Tyr Ser Ser Glu Leu Glu Lys His Gln Leu Tyr
                20                  25                  30

Ile Asp Glu Thr Val Asn Ser Asn Ile Pro Thr Asn Leu Arg Val Leu
            35                  40                  45

Arg Ser
    50

<210> SEQ ID NO 5
<211> LENGTH: 37
<212> TYPE: PRT
<213> ORGANISM: Homo sapiens

<400> SEQUENCE: 5

Asp Asn Glu Asn Val Val Asn Glu Tyr Ser Ser Glu Leu Glu Lys His
1               5                   10                  15

Gln Leu Tyr Ile Asp Glu Thr Val Asn Ser Asn Ile Pro Thr Asn Leu
                20                  25                  30

Arg Val Leu Arg Ser
            35

<210> SEQ ID NO 6
<211> LENGTH: 28
<212> TYPE: PRT
<213> ORGANISM: Homo sapiens

<400> SEQUENCE: 6

Ser Ser Glu Leu Glu Lys His Gln Leu Tyr Ile Asp Glu Thr Val Asn
1               5                   10                  15

Ser Asn Ile Pro Thr Asn Leu Arg Val Leu Arg Ser
                20                  25